(12) United States Patent
Deterre (10) Patent No.: US 10,980,997 B2
(45) Date of Patent: Apr. 20, 2021

(54) PHOTOSENSITIVE PIXEL WITH SHUNT RESISTOR

(71) Applicant: PIXIUM VISION SA, Paris (FR)

(72) Inventor: Martin Deterre, Paris (FR)

(73) Assignee: PIXIUM VISION SA, Paris (FR)

( * ) Notice: Subject to any disclaimer, the term of this patent is extended or adjusted under 35 U.S.C. 154(b) by 395 days.

(21) Appl. No.: 15/573,696

(22) PCT Filed: Apr. 28, 2016

(86) PCT No.: PCT/EP2016/000690
§ 371 (c)(1),
(2) Date: Nov. 13, 2017

(87) PCT Pub. No.: WO2016/180517
PCT Pub. Date: Nov. 17, 2016

(65) Prior Publication Data
US 2018/0064929 A1    Mar. 8, 2018

(30) Foreign Application Priority Data

May 12, 2015  (EP) .................................. 15001427

(51) Int. Cl.
*A61N 1/05*  (2006.01)
*A61N 1/36*  (2006.01)

(52) U.S. Cl.
CPC ....... *A61N 1/0543* (2013.01); *A61N 1/36046* (2013.01)

(58) Field of Classification Search
None
See application file for complete search history.

(56) References Cited

U.S. PATENT DOCUMENTS

2005/0131490 A1   6/2005  Palanker
2012/0153423 A1*  6/2012  Lee ..................... H01L 27/1446
                                                              257/446

OTHER PUBLICATIONS

Boinagrov David et al, "Photovoltaic Pixels for Neural Stimulation: Circuit Models and Performance", IEEE Transactions on biomedical circuits and systems, IEEE, Feb. 2016, pp. 85-97, vol. 10, No. 1, US.
Lorach Henri et al, "Photovoltaic restoration of sight with high visual acuity", Nature Medicine, Apr. 27, 2015, pp. 476-482, vol. 21, No. 5.
PCT/EP2016/000690, Jul. 29, 2016, International Search Report / Written Opinion.
Wang, L et al:"Photovoltaic retinal prosthesis: implant fabrication and performance", J Neural Eng. Aug. 2012; 9(4): 046014. Published online Jul. 12, 2012. doi: 10.1088/1741-2560/9/4/046014.

* cited by examiner

*Primary Examiner* — Michael W Kahelin
*Assistant Examiner* — Elizabeth K So
(74) *Attorney, Agent, or Firm* — Workman Nydegger (57) ABSTRACT

The present invention relates to a photosensitive implant comprising at least one pixel (10) having at least one diode (12, 12'), a stimulating electrode (14), a counter electrode (18), and a resistor (16), wherein the resistance of the resistor (16) is chosen according to a predetermined relation of resistance, a size of the stimulating electrode (14), and a size of the diode (12, 12'). Further, the present invention concerns a method to provide such an implant.

22 Claims, 10 Drawing Sheets

PHOTOSENSITIVE PIXEL WITH SHUNT RESISTOR

The present invention relates to a photosensitive implant with at least one photosensitive pixel.

Implant systems are known, which help to restore at least a fraction of vision to patients who have lost sight, for instance through degenerative diseases such as Retinitis pigmentosa. Vision may at least to a certain degree be restored with an implant by exploiting the fact that the degenerated tissue of the retina may be bypassed and that the retina may still be stimulated directly. This electrical stimulation can be provided by means of an implant system. Such a system typically comprises special goggles, which are placed in front of an eye of a patient and an implant, in particular a sub-retinal implant, which comprises a plurality of electrodes.

In the goggles, typically a camera is provided. The camera is adapted to capture a scene in front of the patient. This captured scene is translated from visual information into a predetermined IR light pulse signal. The implant is adapted to receive those IR light pulses and, in response, the implant is stimulated based on the scene content received by the camera. The implant then converts light into electrical current that stimulates the residual cells in the retina.

For that purpose, the implants comprise a pixel array, wherein each pixel comprises one or more diode areas, a stimulating electrode and a counter electrode. The stimulation electrode is typically arranged in the center of the pixel. Trenches are provided between the individual diodes of a pixel and between the pixels in order to isolate those specific areas from one another. Electrical connections between the diodes and the electrodes are provided to interconnect the components.

If an IR pulse is directed to a pixel or rather to a photosensitive area of a pixel, an electrical pulse is generated by the photodiode circuit in response thereto.

Wang et al. (Photovoltaic retinal prosthesis: implant fabrication and performance; J Neural Eng. 2012 August; 9(4)) describe that the addition of a shunt resistor will help to speed up the discharge phase of the stimulation wave form. Loudin et al. (IEEE transactions on biomedical circuits and systems; volume 5) suggest the use of a shunt resistor for photodiode circuits in retinal prostheses. Similarly, Mandel et al. (Cortical responses elicited by photovoltaic sub-retinal prostheses exhibit similarities to visually evoke potentials; Nature Communications) and Boinagrov et al. (Photovoltaic Pixels for Neural Stimulation: Circuit Models and Performance; IEEE) refer to optically-activated neurostimulation by means of sub-retinal arrays of photovoltaic pixels. Mathieson et al. (Photovoltaic retinal prosthesis with high pixel density; nature photonics) also describe a retinal prosthesis system with sub-retinal photodiode arrays.

In order to reliably stimulate residual cells, on the one hand, the current density, i.e., the charge, which is actually delivered per phase per electromagnetic pulse, e.g. per IR pulse in a predetermined time, should be as high as possible in order to sufficiently stimulate residual cells. On the other hand, the current density should not be too high. Otherwise, tissue damage or damage to the electrode may occur. Further, the voltage across the individual electrode should not surpass the hydrolysis limits, since otherwise the surrounding water will dissociate. Again, potential damage to the surrounding tissue as well as electrode degradation may be the consequence thereof. Further, the voltage applied to the electrodes of the implant should ideally fall back to zero volt after a stimulation pulse and prior to any subsequent pulses, to allow positive and negative charges applied by the implant to be balanced. Otherwise, electrodes could deliver some residual DC current which could damage the surrounding tissue as well as the electrode itself. Prior art systems thus fail to either provide a high charge or to allow satisfying charge balancing, or both. Further drawbacks of prior art systems may be found in that the photosensitive area of diodes in a pixel of the implant often are not ideally fitted to the size and the capacity of an electrode of that pixel.

It is therefore an object of the present invention to provide an implant, which omits at least one of the disadvantages of prior art systems, while allowing enhanced charge delivery.

In particular, it is an object of the present invention to provide an implant having an optimized structure with respect to photosensitive and electrode sizes in order to enhance charge delivery.

It is further known that implants with electrode arrays according to the present invention comprise an electrode, i.e. a stimulating or working electrode, and a counter electrode, also referred to as return electrode, with an additional resistor provided in an electrical circuit between the electrodes. This additional resistor also may be referred to as shunt resistor. The shunt resistor allows the charge delivered during the first phase of the IR pulse to be rapidly discharged and to control the charge, which is actually delivered to the tissue. If the shunt resistor has a high resistance or if there is no shunt resistor, the charge delivered during the first phase of the pulse may not rapidly discharge. Therefore, the time for the voltage to fall down to zero increases. Possibly, charges could not be balanced sufficiently quick prior to a further pulse. A high resistance of the shunt resistor therefore could limit the capacitance available for the next pulse and therefore the delivered charge in steady state would be reduced.

On the other hand, a low resistance of the shunt resistor would allow the charge to discharge rapidly and fully, but a significant fraction of the photogenerated charge would be lost in the shunt resistor and the charge delivered to the tissue would be reduced.

It is therefore a specific object of the present invention to provide an ideally dimensioned shunt resistor for the specific design chosen for the electrode and diode.

The problem is solved according to the invention with a device according to independent claim 1. Advantageous developments are subject-matter of the dependent claims. Further, the problem is solved by a method according to claim 16.

A photosensitive implant according to the present invention comprises at least one pixel having at least one diode, a stimulating electrode, a counter electrode and a resistor which is provided between the stimulating electrode and the counter electrode. The resistor therein is preferably electrically connected in parallel to the diode or to multiple diodes of the pixel. The resistance of the resistor is determined according to a predetermined relation of resistance, a size of the stimulating electrode, and a size of the at least one diode.

With respect to the present invention, it is referred to a photosensitive implant as the most preferred embodiment of the present invention. That structure representing the implant may, in alternative embodiments, be provided as a substrate carrying at least one diode, a stimulating electrode, a counter electrode and a resistor, while that substrate is not implanted. In such embodiments, photogenerated charges of the diode or diodes may excite the stimulating electrode in order to create an electrical field with highly defined field distribution. That may, for instance, allow stimulation of tissues from outside of a body or the stimulation of other structures separate from a tissue.

By correlating the resistance of the resistor depending on its relation to the size of the stimulating electrode and the size of the at least one diode, the inventors are enabled to provide an implant, wherein the shunt resistor is optimally adapted to provide a maximum charge, while, at the same time, enabling for reliable charge balancing. This may allow provision of implants, which are fitted for multiple parameters, due to the predictable shunt resistor value depending on electrode size and diode size.

The pixel size herein shall be understood as the pitch between two neighboring pixels. A "size" of pixel, electrode or diode, among others, in the context of the application may refer to any measure that allows a characterization of the dimensions of that component, either in relation to one another or in absolute numbers. In more specific embodiments, the size of either of the components according to the present invention may for instance be represented by a surface area, visible area, active area or others of that component.

Even though the present invention according to preferred embodiments of the invention refers to an implant, in which a shunt resistor is provided, the inventive idea to provide the electrode and the diode in a specific, predetermined relation of their respective sizes, may also be applied for those cases, in which no shunt resistor is provided in the pixel (i.e., a resistor with infinite resistance).

The choice of size for the electrode, the diode or the resistance of the resistor is influenced by a couple of factors, as already indicated. For an electrode size, which is adapted, preferably optimally adapted, for charge input, the charge density of an electrode with that nominally optimal electrode size may, however, exceed the values for electrode degradation and/or tissue damage. In some embodiments of the present invention, the electrode size therefore may have up to twice the size of an otherwise optimum electrode size. Increased electrode size may reduce the charge density and therefore can help to reduce the risk of damaging tissue or electrode.

It will be understood that a photosensitive implant according to the invention, comprising stimulating electrodes, is adapted to stimulate biological cells or tissue. In particular, stimulation of neural cells, such as neurons, or various kinds of tissue of a body may be accomplished. The photosensitive implant, for that purpose, may be implanted in a tissue. The electrodes, in particular the stimulating electrodes, of the implant may be arranged and positioned such that an electrical pulse on a stimulating electrode may stimulate one or more cells in the surrounding tissue. The electrodes may also be provided such that they directly contact one or more cells of the tissue surrounding the implant.

With that respect, basically, any neural tissue, nerves or cells may be stimulated by the implant. In particular, the implant may be a retinal implant, an implant of the brain, a heart implant or an implant for any other living tissue such as of the ear, in particular the inner ear, or muscles among others, which may be electrically stimulated. According to the invention, an electrical charge is generated by a pixel according to the present invention on a stimulating electrode upon detection of a sufficient light stimulus by the photoactive pixel area, i.e., on the diode or diodes of the pixel. Thus, any position within a tissue may be suitable to receive the implant, provided a light excitation of at least one diode, and thus the stimulating electrode connected with that diode, may be realized.

Such excitation by light through the diode on a pixel may be applied by an external light source, i.e. a light source external to the body, in which the implant is provided. Alternatively, a light source may be provided by a further implant or through further means, from within the body, in which the implant is provided. In particular, infrared light or light pulses may be used to illuminate the photosensitive area of a pixel. Such IR light may also be adapted to penetrate through several layers of tissue, in particular a skin of a patient carrying the implant or further tissue layers, e.g. from outside of an organ or living tissue to be stimulated.

According to a development of the present invention, the size of the stimulating electrode and the size of the diode is represented by an area of the stimulating electrode and an area of the diode, respectively. That means, the resistance of the shunt resistor is dependent on both, an area of the stimulating electrode and an area of the diode, in particular on a relation of the areas of the stimulating electrode and of the diode. This may allow a better measure for the actual dimensions and geometries typically used for the electrode and the diode. Notably, the area of the diode preferably refers to an area of a photosensitive portion of the diode area, i.e., an active diode area. Similarly, the area of the electrode preferably refers to an active electrode area. One or more diodes, the electrode and/or the entire pixel may therefore also be applied with non-symmetric or arbitrary shapes according to the invention.

In a further development of the present invention, in one pixel, a plurality of diodes, such as two diodes or three diodes, are provided. The diode size referred to in relation to the electrode size and the resistance of the resistor advantageously is an effective diode size. That effective diode size may preferably be defined as a ratio of a total diode size divided by the number of diodes in the pixel. Thus, the effective diode size is a measure for an average diode size within the pixel. That definition is in particular appropriate in a case where a plurality of diodes on a pixel have the same or similar size. That can allow a better characterization of the structural parameters of the pixel or of the implant in general. In some embodiments, a pixel contains more than one diode, wherein, accordingly, the individual diodes of the pixel may be equal or at least similar in size. It is, however, also possible, that the individual diodes of the pixel differ in size or that at least one diode differs in size from the remaining diodes. This may allow a more elaborate tuning of the electrical properties of the implant and thus may result in better performance of the implant. In particular in such cases, other definitions for an effective diode size, such as the size of the smallest of the diodes, in particular of serially connected diodes, or such as a weighted average with respect to the diode position on the pixel and the diode shape, or similar, are also possible.

By considering the true geometry of the diode or diodes and the electrode, i.e. of the actual geometry of a pixel as a whole, a more accurate prediction of performance and the provision of a better suited resistor may be enabled. This may further enhance the functionality of the implant.

In some embodiments, an electrode area may be up to 100000 $\mu m^2$ or even more. In some embodiments, the electrode area may be between 5 and 10 $\mu m^2$. In more preferred embodiments, the electrode area is 20 $\mu m^2$ or more, more preferably 50 $\mu m^2$ or higher, in particular 100 $\mu m^2$ or higher. In even more preferred embodiments, the electrode area is between 100 $\mu m^2$ and 10000 $\mu m^2$. Most preferably, the electrode area is between approximately 500 $\mu m^2$ and 3300 $\mu m^2$. A smaller electrode size may allow contacting of smaller regions of the tissue or individual cells.

An increased electrode area may allow easier manufacturing. A pixel comprising an electrode with an area of 5 µm² may for instance have a total pixel area of about 20 µm². Accordingly, independent of the absolute size of the pixel, the electrode size may in some embodiments be between 2% and 50% of the pixel size, preferably between 5% and 20%, more preferably between 10% and 15%. In particular embodiments, the electrode size may be 12.5% of the pixel size. Notably, the above limits may apply also in a particular case, where the size represents the area of the electrode and the pixel, respectively.

Accordingly, a diode area may be up to 100000 µm². In specific embodiments diodes may have an area between 50 µm² and 100000 µm². In some embodiments, the diode area is higher than 100 µm², preferably equal to or higher than 200 µm². In preferred embodiments of the present invention, the diode area is between 500 µm² and 10000 µm².

It is to be noted that the size, i.e. the area, of the diode and of the electrode may be varied widely within the scope of protection of the present invention. Upper limits for the size of either electrode or diode may be set by physiological conditions of an eye, into which an implant according to the present invention is to be implanted. Similarly, a lower limit for the size, i.e., the area of the electrode or diode may be set by technical limits, i.e. to produce reliable structures on the order of few square-microns or below.

In an embodiment of the present invention, the predetermined relation of the resistance of the resistor is determined by the relation of the diode size to the electrode size according to the relation:

$$R \sim D^m \cdot E \qquad \text{(Eqn. 1)}$$

wherein R is the resistance of the shunt resistor in [kOhm], D is the diode size in [µm], E is the electrode size in [µm] and m is an exponent.

In preferred embodiments of the present invention, the above relation according to equation (1) may be represented in more detail by the relation according to equation (2):

$$R = a \cdot D_{area}^n E_{area} \qquad \text{(Eqn. 2)}$$

$$[\text{kOhm}] = [\text{kOhm} \cdot \mu m^{-2(n+1)}] \cdot [(\mu m^2)^n] \cdot [\mu m^2] \qquad \text{(Eqn. 2a)}$$

wherein R is the resistance of the shunt resistor in [kOhm], $E_{area}$ is the effective electrode area of the electrode in [µm²], $D_{area}$ is the effective diode area of the diode in [µm²], n—as well as m in Eqn. (1) above—is an exponent, and a is a constant.

It should be noted that the parameters a and n have dimensions in correspondence with the dimensions of the physical parameters of the respective pixel, the pixel array and the implant, as suggested by Eqn. (2a) above. In the case of Eqn. (2), the exponent n is dimensionless. It will however be understood that the present approach is not a mathematical description of a pixel or of its properties. Rather, Equations (1) and (2) above allow to define implants having pixels or a pixel array with specific technical properties, which may be best reflected with the parameters indicated above. That includes that the constant a, depending on the magnitude of the exponent n may have non-integer dimensions. So far, the inventors could not come up with a satisfying physical explanation of this phenomenon. This, however, has no influence on the suitability of the parameters to define the present invention, i.e. the implant and, in particular, the technical properties of the at least one pixel or an entire pixel array.

The exponent n and the constant a generally determine the interrelation between diode size, electrode size and resistance. It is the finding of the inventors of the present invention that devices designed according to these parameters, which each determine a parameter set for pixel size, diode size and resistance of the resistor, are advantageous over the vast amount of possible other, arbitrary sets of parameters. Thus, implants realizing pixels with a relation according to the present invention may be better suited and directed for the specific application. Performance of the respective implants may therefore be increased. In particular, pixels and pixel arrays exhibiting technical features according to parameters defined according to the present invention may in particular be well suited for applications in implants, preferably in retinal implants, to stimulate biological cells or tissue.

That identified relation even provides a way to predict optimal shunt resistors and therefore to facilitate the production of the implants.

In some embodiments of the present invention, the electrode size may be chosen such that, for a predetermined total photosensitive diode area, the ratio between the total photosensitive diode area and the electrode area is between 0.1 and 10, preferably between 1 and 9, most preferably between 3 and 6.

Such pixel structures for an implant according to the invention are particularly advantageous, as they may provide maximized charge density while not decreasing the performance of the electrode in terms of charge balancing.

In some embodiments of the present invention, the electrode size is chosen such that, for a predetermined photosensitive diode area, in the relation between photosensitive diode area and electrode area the constant a is chosen from the interval [3·10⁵; 2·10⁶]. Preferably. The constant a is chosen from the interval [7·10⁵; 1.5·10⁶]. Most preferably, the constant a fulfils a=10⁶.

In some embodiments, the electrode size is chosen such that, for a predetermined photosensitive diode area, in the relation between photosensitive diode area and electrode area the exponent n is chosen from the interval [−1.5; −2]. More preferably the exponent n is chosen from the interval [−1.75; −1.85]. Most preferably, n fulfils n=−1.81.

In particular embodiments of the present invention, the exponent n fulfils n=−1.81 and the constant a is chosen from the interval [3·10⁵; 2·10⁶], preferably from the interval [7·10⁵; 1.5·10⁶].

In further particular embodiments of the present invention, the constant a fulfils a=10⁶ and the exponent n is chosen from the interval [−1.5; −2], preferably from the interval [−1.75; −1.85].

Such choices of parameters may allow a facilitated production process adapted to a variety applications.

Implants having a shunt resistor characterized by such values for the constant a and/or the exponent n are advantageous in fulfilling multiple requirements of an implant such as charge injection and charge balancing. Attempts so far, at best, were directed at enhancing the characteristics of an implant for one of these parameters, only. Thus far, there were no measures at hand that would allow a multi-parameter assessment. The present invention may therefore allow to provide devices, which are implants with enhanced functionality when connected with living tissue.

As is known to those skilled in the art, the exact values of size and resistance still comprise tolerances. That is due to the fact that further parameters, which are not viable to the scope of the present invention, may require further compromises regarding the final structure of the implant. The mentioned advantageous developments of the present invention thus provide a range of values for acceptable resistance in order to solve the problem of the present invention. That means that for any set of parameters, i.e. diode size and electrode size, a range of acceptable resistance values for the resistor are acceptable within the scope of the present invention.

According to further developments of the present invention, the counter electrode is arranged around the stimulating electrode. In addition or alternatively, the counter electrode may be arranged around the at least one diode. The term "arranged around" in the context of the present invention shall be understood such that the counter electrode has a lateral dimension and, in that lateral dimension, encircles, preferably encircles completely, the area defined by the stimulating electrode or by the at least one diode. In the case that a plurality of diodes is provided, the counter electrode may be arranged around one or all of the diodes. With this arrangement, an improved light detection and stimulation process may be established with homogeneous field distribution of the electric field created by the stimulating electrode. It is also possible that the counter electrode is arranged only partially around the pixel or the photosensitive area or the stimulating electrode.

The implant according to an embodiment of the invention may comprise a plurality of pixels. The plurality of pixels may be arranged in a pixel array, in particular in a way that the space available on a substrate of the implant is optimally used. This is typically achieved by providing the individual pixels in a hexagonal shape such that one pixel is adjacent to six further surrounding pixels. That way, the implant may be provided with increased resolution.

The width of the counter electrode, in the case of an annular hexagonal grid at the periphery of each pixel, could for instance range from 1% to 30% of the pixel size. Preferably, in the range of 5 µm to 25 µm.

Notably, in the embodiments according to the present invention, the photodiodes can be connected to the active electrode and to the counter electrode with either anodal or cathodal polarities.

In a preferred embodiment, the photosensitive implant is a sub-retinal implant. That allows to implant the implant within the eye of a patient, i.e. sub-retinally, in order to bypass any damaged tissue of the retina. Consequently, the electrical impulses may be generated in close proximity to the sensitive neural cells which are still functional in the retina. Alternatively, the implant may be an epiretinal implant.

A further aspect of the present invention refers to a method for producing such a photosensitive implant. The method comprises at least the steps of providing a substrate, providing, on the substrate, a pixel structure. That pixel structure comprises at least an electrode, a diode and a resistor. The resistance of the resistor is chosen according to a predetermined relation of resistance, a size of the stimulating electrode, and a size of the diode. In order to provide an implant for implantation in or on a retina or different tissue, for instance, a pixel array consisting of a plurality of pixels on a substrate may be provided. Production may be conducted similar to techniques available for semiconductor production.

The method may further comprise providing at least one or more trenches on the pixel and/or on the pixel array. The trenches may be provided in order to electrically isolate specific regions of the pixel and/or the pixel array from one another, For instance, a trench may be provided between different diodes provided on one pixel. Further, a trench may be provide to electrically isolate the stimulating electrode or one or more diodes from a counter electrode surrounding the pixel. A trench may also be provided in order to electrically isolate one or more regions of the pixel array from other regions of the pixel array or from centrally provided counter electrodes.

The choice of parameters and parameter sets during production of the implant may be according to the above indicated considerations.

As has been outlined before, the size of the stimulating electrode and the size of the diode is represented by an area of the stimulating electrode and an area of the diode, respectively. That means, the resistance of the shunt resistor is dependent on both, an area of the stimulating electrode and an area of the diode, in particular on a relation of the areas of the stimulating electrode and of the diode. This may allow a better measure for the actual dimensions and geometries typically used for the electrode and the diode. Notably, the area of the diode preferably refers to an area of a photosensitive portion of the diode area, i.e., an active diode area. Similarly, the area of the electrode preferably refers to an active electrode area. One or more diodes, the electrode and/or the entire pixel may therefore also be applied with non-symmetric or arbitrary shapes according to the invention.

Preferably, the diode size referred to in relation to the electrode size and the resistance of the resistor advantageously is an effective diode size. That effective diode size may preferably be defined as a ratio of a total diode size divided by the number of diodes in the pixel. Thus, the effective diode size is a measure for an average diode size within the pixel. That definition is in particular appropriate in a case where a plurality of diodes on a pixel have the same or similar size.

In an embodiment of the inventive method, the predetermined relation of the resistance of the resistor is determined by the relation of the diode size to the electrode size according to the relation:

$$R \sim D^m \cdot E \qquad \text{(Eqn. 1)}$$

wherein R is the resistance of the shunt resistor in [kOhm], D is the diode size in [µm], E is the electrode size in [µm] and m is an exponent.

Preferably, the above relation according to equation (1) may be represented in more detail by the relation according to equation (2):

$$R = a \cdot D_{area}^n E_{area} \qquad \text{(Eqn. 2)}$$

$$[kOhm] = [kOhm \cdot \mu m^{-2(n+1)}] \cdot [(\mu m^2)^n] \cdot [\mu m^2] \qquad \text{(Eqn. 2a)}$$

wherein R is the resistance of the shunt resistor in [kOhm], $E_{area}$ is the effective electrode area of the electrode in [µm$^2$], $D_{area}$ is the effective diode area of the diode in [µm$^2$], n—as well as m in Eqn. (1) above—is an exponent, and a is a constant.

In some embodiments of the inventive method, the electrode size is chosen such that, for a predetermined photosensitive diode area, in the relation between photosensitive diode area and electrode area the constant a is chosen from the interval [3·10$^5$; 2·10$^6$]. Preferably. The constant a is chosen from the interval [7·10$^5$; 1.5·10$^6$]. Most preferably, the constant a fulfils a=10$^6$.

In some embodiments of the inventive method, the electrode size is chosen such that, for a predetermined photosensitive diode area, in the relation between photosensitive diode area and electrode area the exponent n is chosen from the interval [−1.5; −2]. More preferably the exponent n is chosen from the interval [−1.75; −1.85]. Most preferably, n fulfils n=−1.81.

In particular embodiments of the inventive method, the exponent n fulfils n=−1.81 and the constant a is chosen from the interval [3·$10^5$; 2·$10^6$], preferably from the interval [7·$10^5$; 1.5·$10^6$].

In further particular embodiments of the inventive method, the constant a fulfils a=$10^6$ and the exponent n is chosen from the interval [−1.5; −2], preferably from the interval [−1.75; −1.85].

In some embodiments of the inventive method, an electrode area may be up to 100000 μm$^2$ or even more. In some embodiments, the electrode area may be between 5 and 10 μm$^2$. In more preferred embodiments, the electrode area is 20 μm$^2$ or more, more preferably 50 μm$^2$ or higher, in particular 100 μm$^2$ or higher. In even more preferred embodiments, the electrode area is between 100 μm$^2$ and 10000 μm$^2$. Most preferably, the electrode area is between approximately 500 μm$^2$ and 3300 μm$^2$. A smaller electrode size may allow contacting of smaller regions of the tissue or individual cells.

Accordingly, a diode area may be up to 100000 μm$^2$. In specific embodiments diodes may have an area between 50 μm$^2$ and 100000 μm$^2$. In some embodiments, the diode area is higher than 100 μm$^2$, preferably equal to or higher than 200 μm$^2$. In preferred embodiments of the present invention, the diode area is between 500 μm$^2$ and 10000 μm$^2$.

Further details, preferred embodiments and advantages of the present invention will be found in the following description with reference to the drawings, in which.

Figure 1:
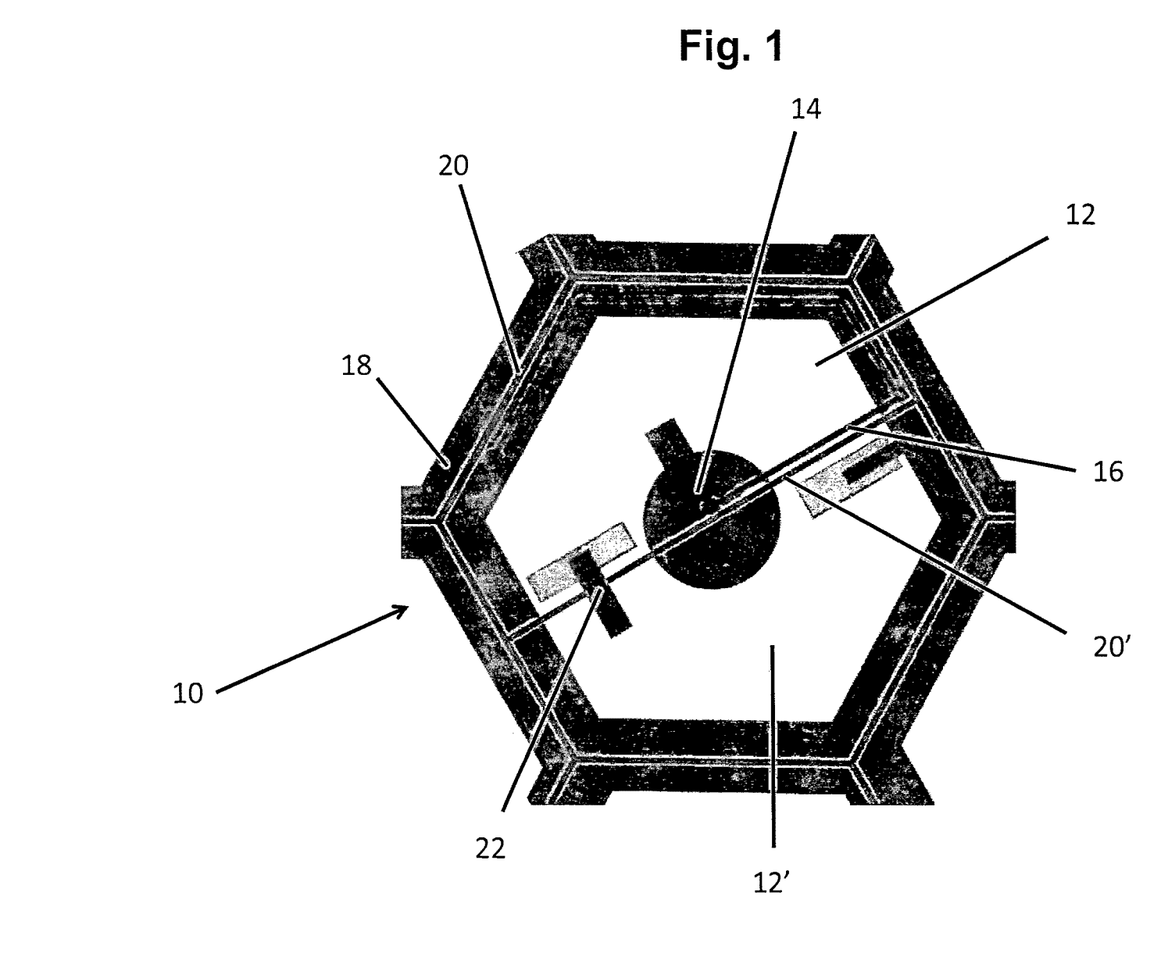
FIG. 1 is an example of a photosensitive pixel with an electrode according to one embodiment of the present invention.

FIG. 1 shows a photosensitive pixel 10 according to an embodiment of the present invention. The photosensitive pixel 10, in the following referred to as a pixel, comprises a photosensitive diode 12, a central electrode 14 and a resistor 16. At an outer periphery of the pixel, a counter electrode 18 is provided, which is also often referred to as return electrode. The counter electrode 18 can be placed on each pixel, for instance at the periphery of each pixel, as shown in FIG. 1. That means, the return electrode is local and in-between the different central electrodes of a pixel array. This is typically also referred to as a "bipolar" configuration.

For such a bipolar arrangement, two configurations are possible. The return electrodes may be disconnected from one another. That means, pixels in that case are completely independent from one another. Alternatively, all return electrodes of individual pixels may be connected together, in order to effectively creating a sort of grid-like structure. That structure may, for instance, have a hexagonal pattern, which may extend over the whole pixel array.

As a further alternative, a central return electrode may be placed separate from the arrangement of central electrodes. Such a central return electrode may in particular be provided at a remote location on the implant. Such a configuration may also be referred to as a monopolar configuration. It is to be noted that the return electrode does not necessarily have to be in a geometrical center of the implant. Further, it is possible that a plurality of such central electrodes are distributed over the implant or the pixel array.

Figure 3:
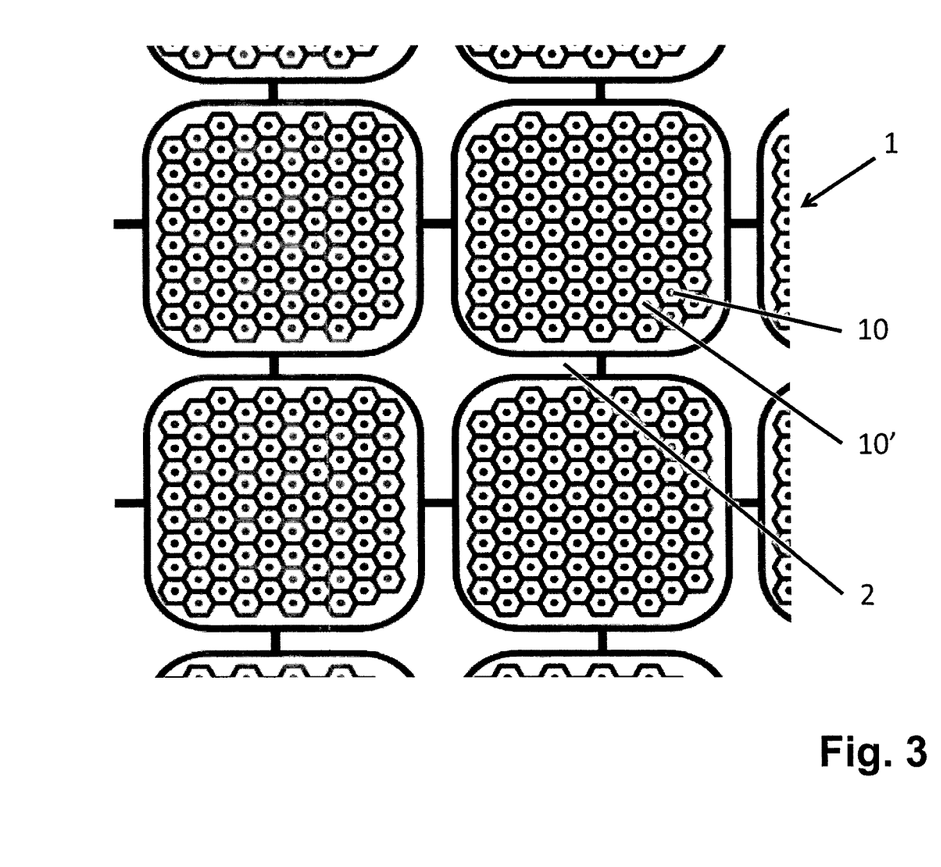
FIG. 3 displays an electrode array according to an embodiment of the present invention.

The pixel 10 in the embodiment as shown in FIG. 1 has a generally symmetric hexagonal shape. Adjacent to each of the sides of that hexagon, further pixels may be provided. An example for one embodiment of an array of pixels, also referred to as an electrode array in the context of the present invention, is shown in FIG. 3. In alternative embodiments, the shape of the individual pixels may also differ. For example, the pixel may have an octagonal or rectangular shape. The pixel may also have circular or diamond shape or any other, even arbitrary shape, without departing from the scope of protection of the present invention.

Individual pixels are separated from each other by means of a trench 20. The trench 20 comprises an electrically isolating material. The individual pixels 1 preferably are electrically isolated from one another. The counter electrode 18 is arranged on the trench 20 surrounding the periphery of the pixel 1 in the embodiment according to FIG. 1.

In the embodiment shown in FIG. 1, the pixel 10 further comprises two diodes 12, 12'. The diodes 12, 12' are arranged inscribed within the area of the hexagonal pixel shape. Preferably, the diodes 12, 12' are symmetrically arranged. Between the diodes 12, 12', an isolating trench 20' is provided. The isolating trench 20' between the diodes 12, 12' has the same properties as the isolating trench 20. The diodes 12, 12' are therefore basically electrically isolated from one another. It is to be understood that despite trenches arranged within the pixel, i.e. the substrate of the photosensitive element, electrical contact between objects separated and isolated by trenches 20, 20' may still be established by means of electrical contacts. In the embodiment according to FIG. 1, for instance, the diodes are connected by an electrical contact 22. As will be further detailed with respect to FIG. 4, the diodes, that way, are serially connected with respect to one another in the embodiment according to FIG. 1.

The diodes 12, 12' represent in the projection view of the embodiment according to FIG. 1 a photosensitive area of the pixel. In that embodiment, the surface area, i.e. the photosensitive area, of the diodes 12, 12' is essentially symmetric around a symmetry axis (not shown) of the pixel 10. In other embodiments, the number of diodes may be different. In particular, there may be only one diode provided. That would allow to increase the photosensitive area of the pixel, as no trenches 20' had to be provided to separate individual diodes within the pixel 10. In further embodiments, three diodes or more than three diodes may be provided in one pixel. If more than two diodes are provided in a pixel 10, the individual diodes may also be serially connected with one another, as already discussed for a two-diode pixel above.

A plurality of diodes, for instance two or three diodes, for one pixel may be provided, if the voltage, as response to the received signal, needs to be increased. The diodes may therefore be serially connected, wherein the voltage of a number N of diodes is the factor N higher than the voltage created by one diode only. On the other hand, an increased number of diodes means that fewer light may be collected by each diode, per pixel. The electrical current created by each of those diodes connected in series may be significantly lower when having a plurality of diodes compared to having only one or a few diodes. Typically, the current in a circuit with N diodes is N times less than the current of one diode. It is therefore a matter of choice, which of the parameters, i.e., current or voltage, is more desirable for an individual application. In the specific case of neural stimulation, the required stimulation parameters may depend on the tissue and the individual neuronal cells to be excited, the position of an implant and even individual specifics of a patient, possibly age, state of disease and general physiological condition.

In the center of the pixel 10, an electrode 14 is provided. Due to its central position, that electrode 14 is also referred to as central electrode. Further, as that electrode typically is used for stimulation, that electrode is also referred to as stimulating electrode. The stimulating electrode 14 in the shown embodiment is provided having a circular shape. The electrode may also have different shapes, such as a shape mimicking the shape of the return electrode 18 or the trench 20 reflecting the contour of the pixel 10. The circular shape of the presently shown embodiment was chosen such that the electrical field from the stimulating electrode 14 may be homogenous. Depending on the intended application, the shape may also include such shapes which allow less homogenous, locally enhanced field distributions.

According to some embodiments of the present invention, the electrode 14 of the pixel 10 shall be adapted for stimulation of surrounding tissue, preferably neural tissue, in particular neural tissue of a retina in vivo. Typically, the electrode comprises platinum, iridium oxide and/or titanium nitride. Alternatively, iridium, platinum iridium, doped diamond or diamond-like carbon or PEDOT:PSS, or other known materials may be used as electrode material. The preferred structure of the electrode material may in particular be a highly porous structure, such as a porous or fractal TiN or platinum structure. Such structures are known and found to be described to be, e.g., "black platinum" or "porous platinum". The thickness of the electrodes may vary from about 100 nm to 3 µm. It is, however, also possible to have an electrode thickness in the range of 10 µm as well, or below 100 nm.

In the embodiment as shown in FIG. 1, the return electrode 18 is provided as an elongate electrode surrounding the pixel and following the contour of the pixels periphery. In alternative embodiments, the return electrode may also comprise a plurality of electrodes, which are distributed around the pixel 10 and around the stimulating electrode 14 in regular or arbitrary distribution. This may in particular be exerted at a peripheral portion of an electrode array 1.

Further, between the stimulating electrode 14 and the counter electrode 18, a resistor 16 is arranged. The resistor 16, also referred to as a shunt resistor, may in particular be provided on the trench between two diodes 12, 12' of the pixel 10, as is shown in more detail in FIG. 2.

Figure 2:
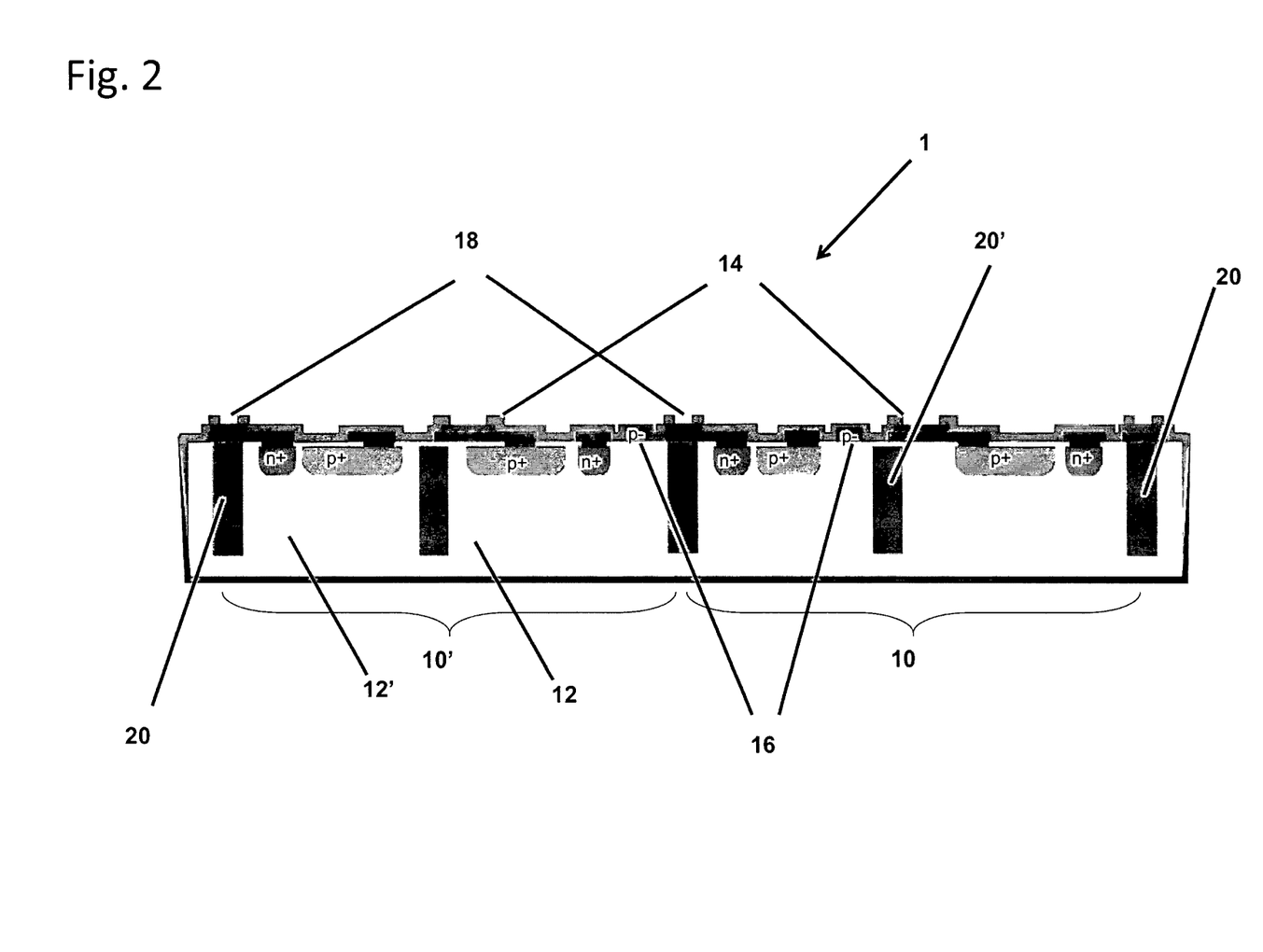
FIG. 2 is a schematic cross-sectional view of a semiconductor structure with two adjacent pixels according to an embodiment of the invention.

FIG. 2 shows a sectional side view of a portion of an electrode array 1, showing two adjacent pixels 10, 10'. The pixels 10, 10' correspond to the pixel according to the embodiment as shown in FIG. 1, having two diodes 12, 12'. The same layer structure as shown in FIG. 1 for a two-diode pixel may essentially also be provided for a one-diode or three-diode pixel, analogously. The resistor 16 herein is provided on a surface of the pixel. According to an embodiment of the invention, the resistor 16 is a conductor on the surface of the pixel 10. In some embodiments, that conductor may be made of or comprise silicon, which was doped, in particular, which was lightly doped. The array 1 is provided on a substrate 2, which may be seen in FIG. 3.

FIG. 3 shows an array of pixels, i.e., an electrode array 1. The electrode array 1 comprises a plurality of pixels 10. The size of the pixels in the electrode array 1 may differ and can thus be tuned to different applications.

Figure 4:
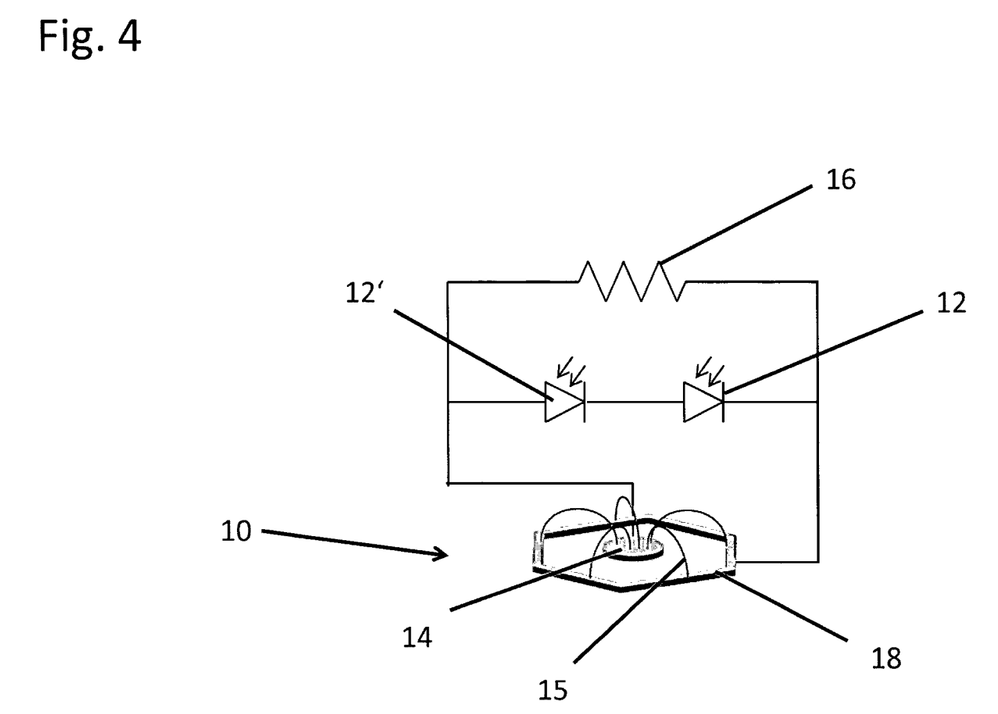
FIG. 4 is a perspective view of the photosensitive pixel of FIG. 1 with a schematic drawing of a wiring circuit.

FIG. 4 shows a schematic perspective view of a pixel 10 according to an embodiment of the present invention. The pixel 10 as shown exhibits the return electrode 20 as a hexagonal elongate electrode. The stimulating electrode 14 is a circular electrode. If electrical voltage is applied, i.e., when the stimulating electrode generates an electrical pulse, an electrical field, represented by the electrical field lines 15 in FIG. 4, is generated. Cells within the proximity of this field may eventually be stimulated, depending on the specifics of the stimulation pulse such as strength, duration polarity, and so forth. The electrode may also be placed in tissue in a way that the tissue, i.e. the cells within the tissue, may directly contact the electrode.

The pixel 10 of FIG. 4 is also provided with two diodes 12, 12', which are serially connected. The resistor 16, i.e. the shunt resistor, is connected in parallel to the diodes 12, 12'. That way, an electrical circuit with reliable charge balancing and stimulation parameters may be established.

Figure 5:
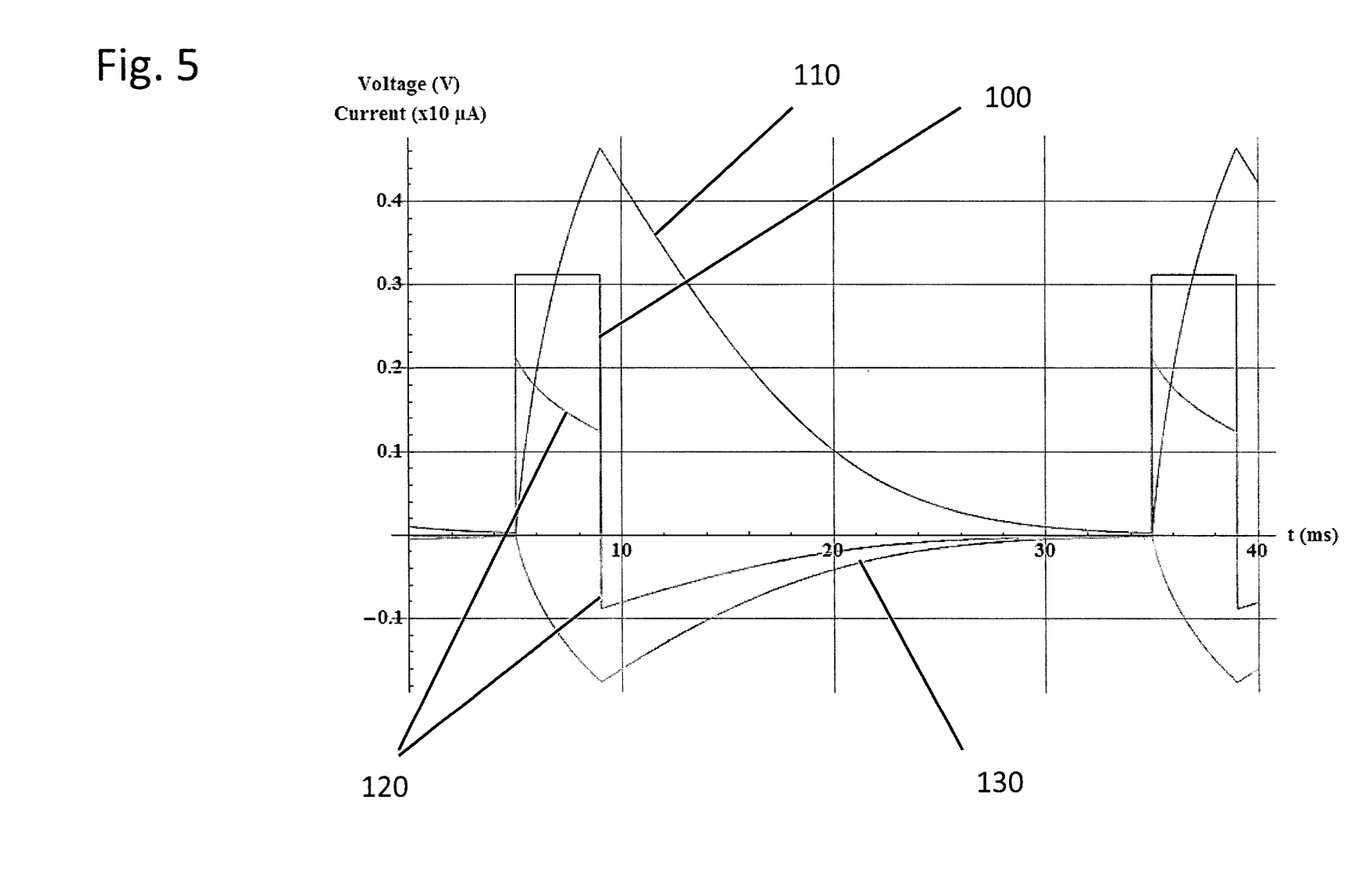
FIG. 5 is a diagram representing a stimulation pulse.

FIG. 5 shows an example of a light pulse 100 on the pixel and a stimulation pulse 110 derived therefrom. Typically, a light pulse on the pixel is an infrared light pulse. The wavelength of the infrared light may be from 750 nm to 3000 nm, preferably between 800 nm and 1000 nm and most preferably between 830 nm and 915 nm. The light pulse typically is a square pulse. Further light pulse shapes may also be exerted, such as a saw tooth profile or a non-linear ramping up and/or down of the light intensity. As soon as a light is detected by one or more of the photosensitive diodes, a current 120 is generated. The longer the light pulse is applied, the higher gets the voltage 110 of the stimulation electrode 14. As the voltage on the active electrode 110 increases in the positive or negative range, the voltage of the counter electrode 130 conversely increases in the negative or positive region, for anodal or cathodal polarity, respectively.

After the light stimulation ceases, the current 120 drops and the voltages of the stimulating electrode and on the return electrode decrease. However, the voltages need time, depending primarily on the resistance of the shunt resistor 16, to equalize. In the example according to FIG. 5, the voltages have dropped to zero only about 26 ms after the light pulse ceased. Only then a next stimulating pulse with full capacitance may be applied by the respective pixel.

The resistance of the resistor 16 significantly influences the function and the performance of the pixel. If a light pulse is received by one of the diodes, i.e. on the photosensitive area, the light pulse is converted into an electrical pulse. The electrical signal is delivered to the stimulating electrode 14. The charge delivered per phase for a light pulse should, ideally, be maximized, in order to increase the stimulation efficacy. The charge density, on the other hand, cannot be too high, in order to prevent tissue damage. Thus, charge densities of between 0.35 mC/cm$^2$ and 1.5 mC/cm$^2$, typically of 1 mC/cm$^2$ are generally chosen. The charge further has to discharge fast enough such that prior to a following pulse, the voltage applied may drop ideally all the way back to zero to balance the charges. This requires a low value resistor. On the other hand, a low value resistor decreases the photogenerated charge that may eventually be used for electrical signal generation.

The present inventors could show that the ideal value of the shunt resistor scales with an area of the stimulating area and of the photosensitive area. In order to define the invention, the embodiments of the present invention, for which protection is sought may be subsumed to fulfil the following equation (1).

$$R \sim D^m \cdot E \qquad \text{(Eqn. 1)}$$

Wherein R is the resistance of the shunt resistor 16, D is the diode size, E is the electrode size and m is an exponent.

In preferred embodiments of the present invention, the above relation may also be described by the relation according to equation (2):

$$R = a \cdot D^n_{area} E_{area} \quad \text{(Eqn. 2)}$$

wherein R is the resistance of the shunt resistor 16 in kOhm, $E_{area}$ is the effective electrode area of the electrode 14 in $\mu m^2$, $D_{area}$ is the effective diode area of the diode 12 in $\mu m^2$, n is an exponent, and a is a constant. That means, the resistance of the resistor 16 is derived from the electrode size and the diode size. In particular, according to these embodiments, the resistance of the resistor 16 is derived from an electrode area and a diode area, preferably an effective diode area. The effective diode area as defined according to the present invention is the light sensitive area of each individual one of the diodes 12, 12', if these are of similar size. It may also be the minimum value of the light sensitive areas of the diodes 12, 12' in a pixel 10.

In the following, an overview shall be provided of the most preferred embodiments of the present invention according to the above definition. It will be apparent to any person skilled in the art that various sets of parameters containing resistance of the shunt resistor, electrode size as well as diode size and diode number may fulfil the requirements indicated in relation to the present invention.

The skilled person will further realize that all values provided herein with respect to absolute or relative relations of parameters or regarding the values of parameters themselves are subject to statistical error and/or to design constraints and variations. Accordingly, values provided should be considered to be representative of values ranging at least +/−25% about that value provided or at least +/−10 $\mu m$, where it is referred to sizes. For instance, a three-diode pixel with a size of 100 $\mu m$, allows optimal values for the electrode size in a range of approximately from 15 $\mu m$ to 30 $\mu m$.

With respect to the shunt resistor values, values may vary more significantly, e.g., from 10% of the represented value up to ten times the optimum value, preferably from 50% of the value up to 5 times the value represented. It will be apparent to those skilled in the art, that for a given setting of parameters, it is the combination of values, i.e. the diode size and number, the electrode size and the resistance, which defines the pixel or pixel array according to the invention.

As will be shown by means of examples for various parameter sets, the findings of the present invention may best be described by means of an exponent n according to the relation −1.5<n<−2. In more preferred embodiments of the present invention, the exponent is chosen between −1.65<n<−1.95, and more particularly between −1.75<n<−1.85. In particular, the exponent n may be n=−1.81.

Tables 1 and 2 provide an overview of the preferred parameter sets according to the present invention in terms of the respective areas in $\mu m^2$ of the electrodes and the diodes. That approach considering the respective areas allows to consider almost arbitrary shapes of the pixels, diodes and the electrodes.

For the parameters set out in Tables 1 and 2, it was identified that, for a preferred exponent n of n=−1.81 the constant a preferably lies between $3 \cdot 10^5 < a < 2 \cdot 10^6$. More preferably the constant a lies between $7 \cdot 10^5 < a < 1.5 \cdot 10^6$. In even more preferred embodiments, the constant a lies between $7.5 \cdot 10^5 < a < 1.25 \cdot 10^6$. The constant a may for instance be $a = 10^6 \pm 20\%$. Most preferably, the constant a is $a = 10^6 \pm 10\%$ in such a setting. Note that the pixel size in [$\mu m$] is a measure as commonly used in order to characterize the pixel. The pixel size itself is not considered for defining the individual characteristics of a pixel in terms of the electrode size (area), diode size (area) and resistance of the resistor. It is further to be understood that the examples provided shall only exemplify the inventive idea to define a pixel or pixel array by means of the resistance of the resistor 16, a size of the electrode 14 and a size of one or more diodes 12, 12'. Specific examples shall not be limiting for the subject-matter as set forth in the claims.

Electrode arrays with pixel-structures according to the parameter sets as set out in Table 1 were optimized for light applied with a power of about 5 mW/mm² and a light pulse duration of about 4 ms.

TABLE 1

Resistance of shunt resistor optimized for light pulses of 4 ms with light power of 5 mW/mm^2

| # of diodes | Pixel size [μm] | Electrode area [μm^2] | Resistance [kOhm] |
|---|---|---|---|
| 1 | 75 | 1650.8 | 520.6 |
| 2 | 75 | 554.8 | 1756.7 |
| 3 | 75 | 255.0 | 1543.0 |
| 1 | 100 | 3408.8 | 283.4 |
| 2 | 100 | 766.7 | 520.6 |
| 3 | 100 | 554.8 | 1296.2 |
| 1 | 140 | 7287.0 | 154.3 |
| 2 | 140 | 1650.8 | 384.1 |
| 3 | 140 | 1314.7 | 520.6 |
| 1 | 280 | 24911.0 | 45.7 |
| 2 | 280 | 7287.0 | 84.0 |
| 3 | 280 | 4536.0 | 113.8 |

Electrode arrays with pixel-structures according to Table 2 were optimized for light applied with a power of about 3 mW/mm² and a light pulse duration of about 4 ms.

TABLE 2

Resistance of shunt resistor optimized for light pulses of 4 ms with light power of 3 mW/mm^2'

| # of diodes | Pixel size [μm] | Electrode size [μm^2] | Resistance [kOhm] |
|---|---|---|---|
| 2 | 75 | 384.2 | 1815.4 |
| 3 | 75 | 255.0 | 3154.8 |
| 1 | 100 | 2907.2 | 345.9 |
| 2 | 100 | 766.7 | 1044.7 |
| 3 | 100 | 384.2 | 1377.1 |
| 1 | 140 | 5828.8 | 209.1 |
| 2 | 140 | 1650.8 | 520.6 |
| 3 | 140 | 1020.0 | 705.6 |

Table 3 displays parameter sets for pixels, which were identified to be a particular advantageous choice of the multitude of possible configurations. The parameter sets as set out in Table 3 were optimized for light applied with a power of about 5 mW/mm² and a light pulse duration of about 4 ms

TABLE 3

Preferred resistance of shunt resistor optimized for light pulses of 4 ms with light power of 5 mW/mm^2'

| # of diodes | Pixel size [μm] | Electrode area [μm^2] | Resistance [kOhm] |
|---|---|---|---|
| 2 | 75 | 384.2 | 1800 |
| 1 | 100 | 1650.8 | 250 |
| 2 | 100 | 766.7 | 900 |
| 3 | 100 | 384.2 | 1200 |

TABLE 3-continued

Preferred resistance of shunt resistor optimized for light pulses of 4 ms with light power of 5 mW/mm^2'

| # of diodes | Pixel size [μm] | Electrode area [μm^2] | Resistance [kOhm] |
|---|---|---|---|
| 1 | 140 | 5828.8 | 130 |
| 1 | 140 | 2447.0 | 130 |
| 2 | 140 | 2907.2 | 450 |
| 2 | 140 | 1650.8 | 400 |
| 3 | 140 | 1020.0 | 600 |

Figure 6:
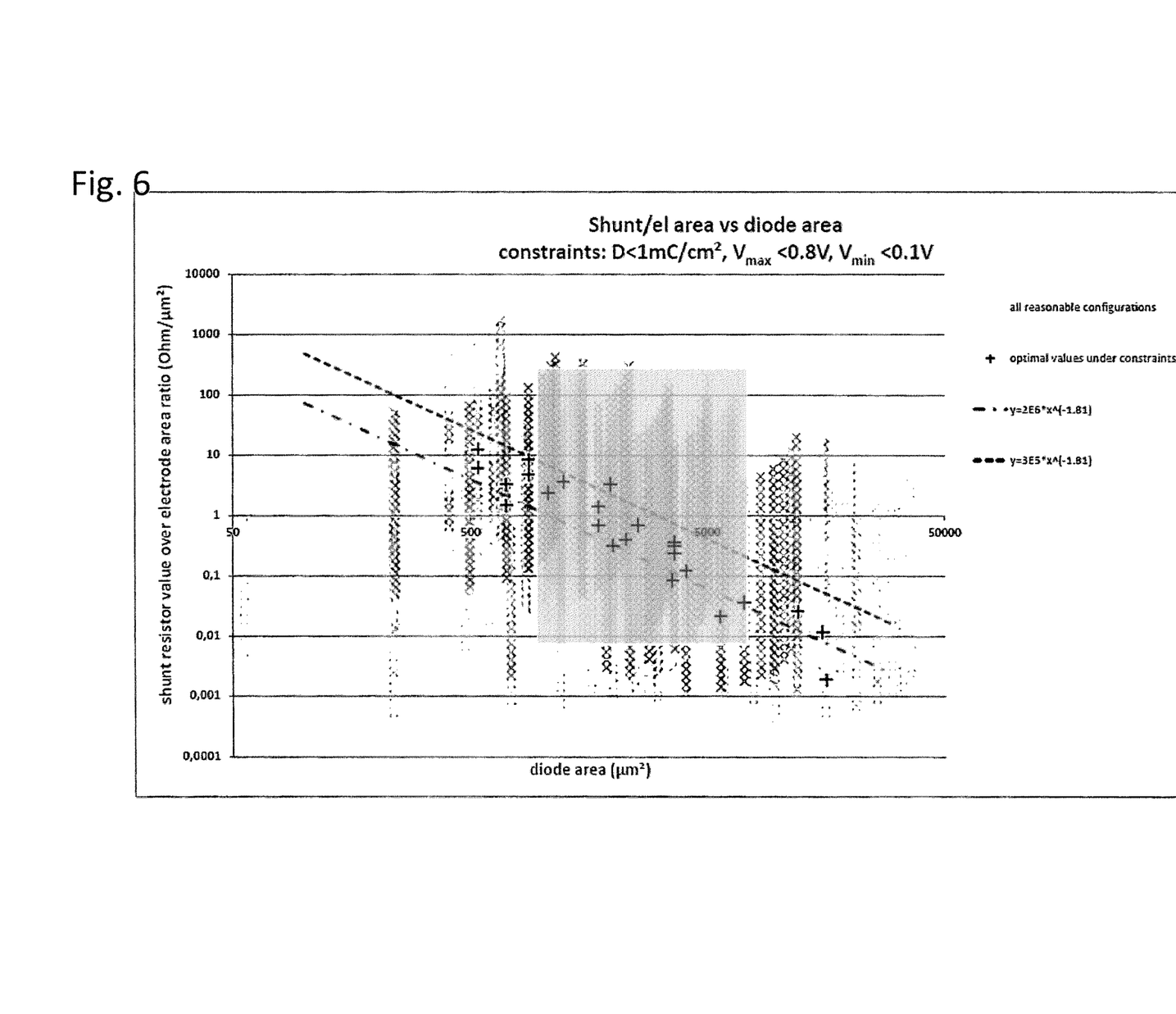
FIGS. 6 to 10 show diagrams for different constraining parameters a and n according to embodiments of the present invention.

FIG. 6 shows a diagram displaying, on a double-logarithmic plot and marked by "x" such parameter configurations for pixels of a pixel array, which are, in generally, reasonable and technically possible. In the diagram, the X-axis represents a size (here, an area) of the diode, e.g., the effective diode area. The Y-axis of the diagram shows the corresponding relation of the shunt resistor value divided by the electrode area derived from Equation (2) as defined above. Those parameter coordinates marked by a "+" in FIG. 6 represent sets of parameters, which are constrained according to the inventive considerations of the present invention.

These constraints may for instance require that the electrode is enabled to provide a specific charge at a specific charge density. That charge density may in particular be about 0.35 mC/cm$^2$. An upper limit of the charge density preferably is at 1 mC/cm$^2$. The charge density may be up to 1.5 mC/cm$^2$. Further these constraints may require that a maximum voltage between the electrode 14 and the counter electrode 18 may not be exceeded in response to a stimulation impulse. In particular, the voltage may be intended to be kept below the hydrolysis voltage of water. As one example considered for the exemplified embodiments according to FIGS. 6 to 10, the maximum voltage may be limited to about 0.8V. A minimal voltage provided by the electrodes on the other hand according to these embodiments for the specific lighting parameters was considered to be less than 0.1V. Moreover, these constraints may, in some embodiments, require that the resistance of the resistor 16 allows a sufficiently fast charge balancing, preferably corresponding to a residual DC current, reflecting an unbalanced charge over time, of less than 0.1 μA, while maximizing the charge available for the stimulation. Reduction of the residual DC current, thus charge balancing the electrodes, may allow more controlled stimulation of tissue and therefore increase the reliability of the pixel or pixel array.

As indicated, those pixels and pixel arrays according to embodiments of the present invention displaying such parameter sets may be described by the above Eqn. (2). In the exemplified embodiment of FIG. 6, the exponent n is n=−1.81. The dotted and the line-dotted lines in FIG. 6 represent an upper and a lower limit of the constant a in Eqn. (2), with the constant a being 3·10$^5$ and 2·10$^6$, respectively. These lines represent straight lines defined by the Equation (2), when rearranged according to the following Equation (3):

$$R/E_{area} = a \cdot D^n_{area} \quad \text{(Eqn. 3)}$$

That definition applies in the same way for the FIGS. 7 to 10 as discussed below.

Figure 7:
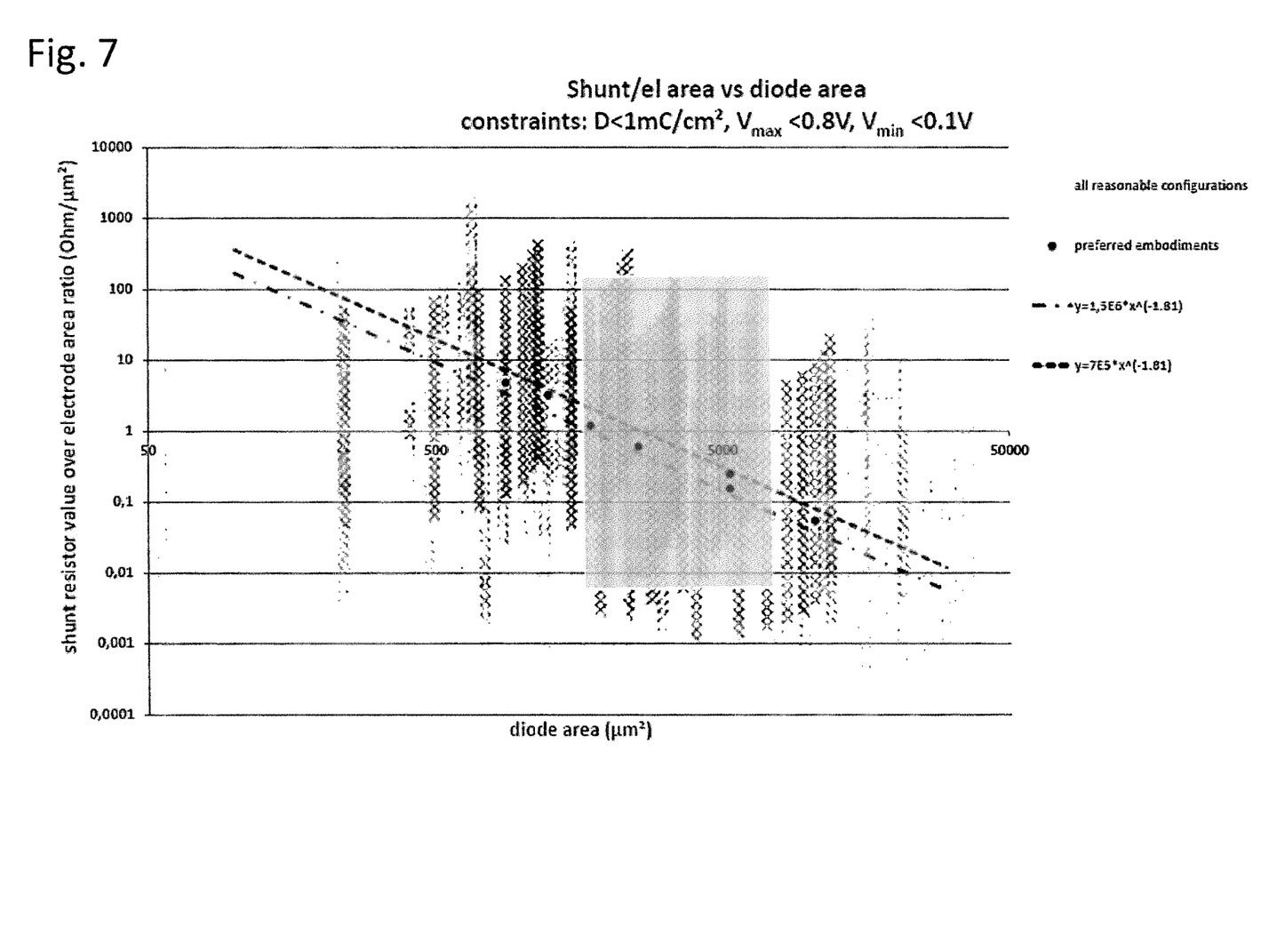

FIG. 7 shows the parameters of further, preferred embodiments of the present invention. These parameter sets are indicated with a black circle (●) in the FIG. 7. As a comparison, FIG. 7 also displays those configurations, which may generally be available as reasonable theoretical configurations. The upper and the lower limits of the embodiments according to FIG. 7 may be defined by a=7·10$^5$ and a=1.5·10$^6$, respectively.

Figure 8:
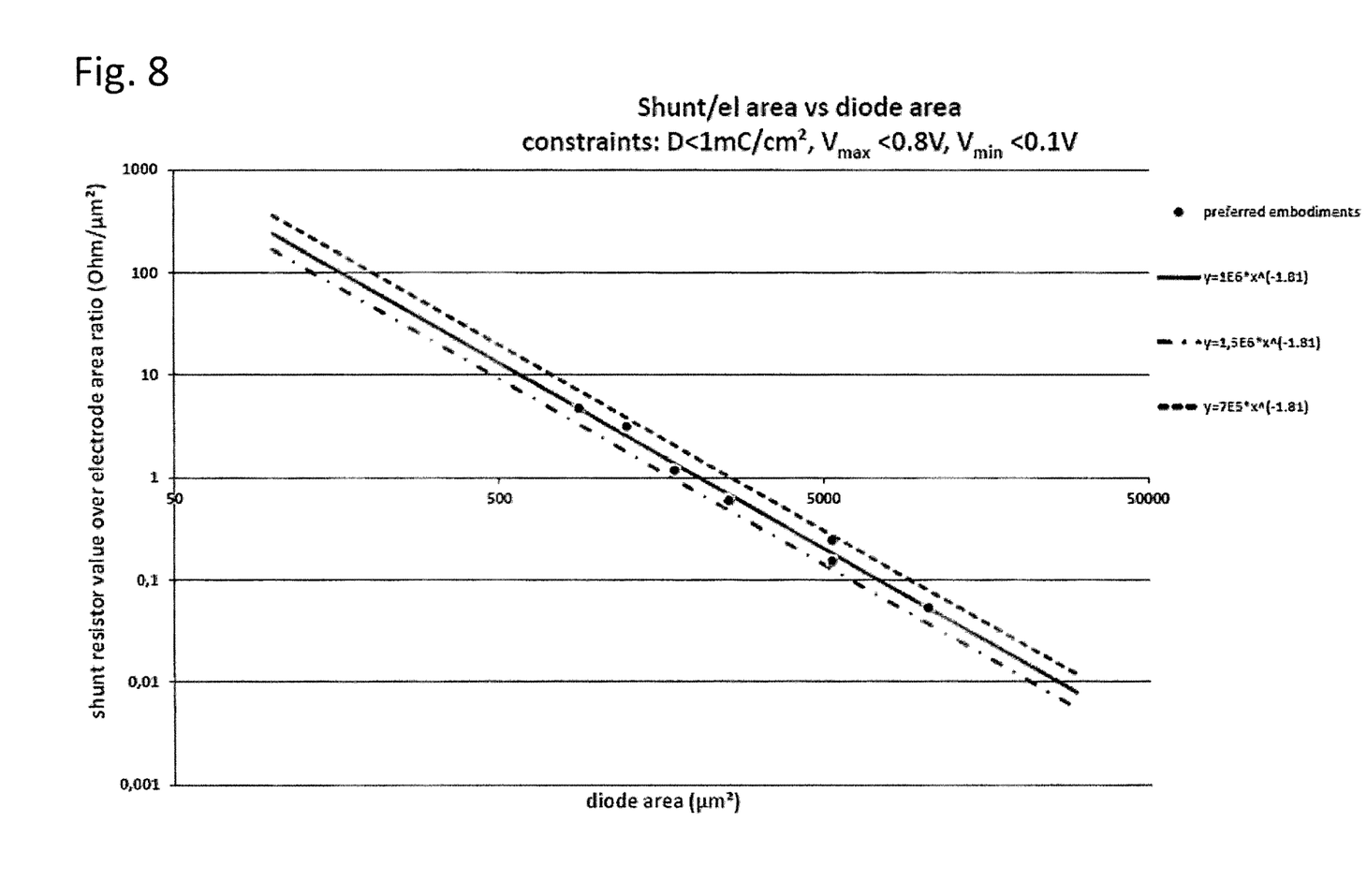

FIG. 8 shows the same diagram as FIG. 7, without displaying all possible parameters sets, and by adding a straight line approximating a preferred center value for the parameter sets of the most preferred embodiments. That line is defined by the constant a=10$^6$ and the exponent n=−1.81. It will be noted that, on the logarithmic plot shown in FIGS. 6 to 10, a common error on the order of 10-50% may be considered as deviation form that preferred central value, without departing from the inventive idea and scope of the present invention.

Figure 9:
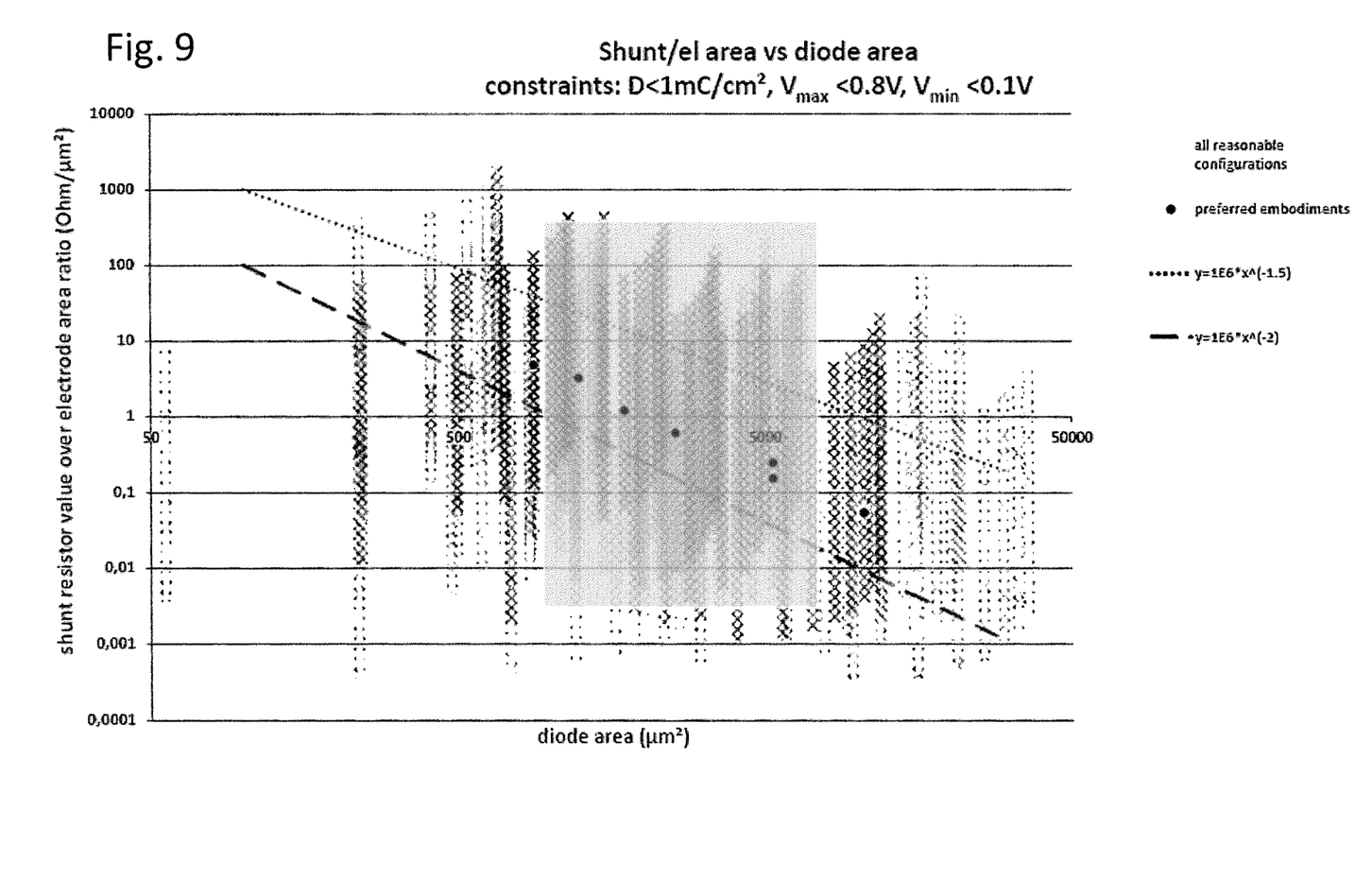

FIG. 9, similarly to FIGS. 6 to 8, shows a diagram of those technical realization, which may theoretically be considered. Further, as in FIGS. 7 and 8, FIG. 9 shows the most preferable embodiments according to the present invention indicated with black circles (●). The lines displayed in FIG. 9, however, indicate an upper and a lower limit of lines defined by above Equation (3), for different exponents n. The exponent for the upper and lower limit of parameter sets in FIG. 9 is defined by n=−1.5 and n=−2, respectively.

Figure 10:
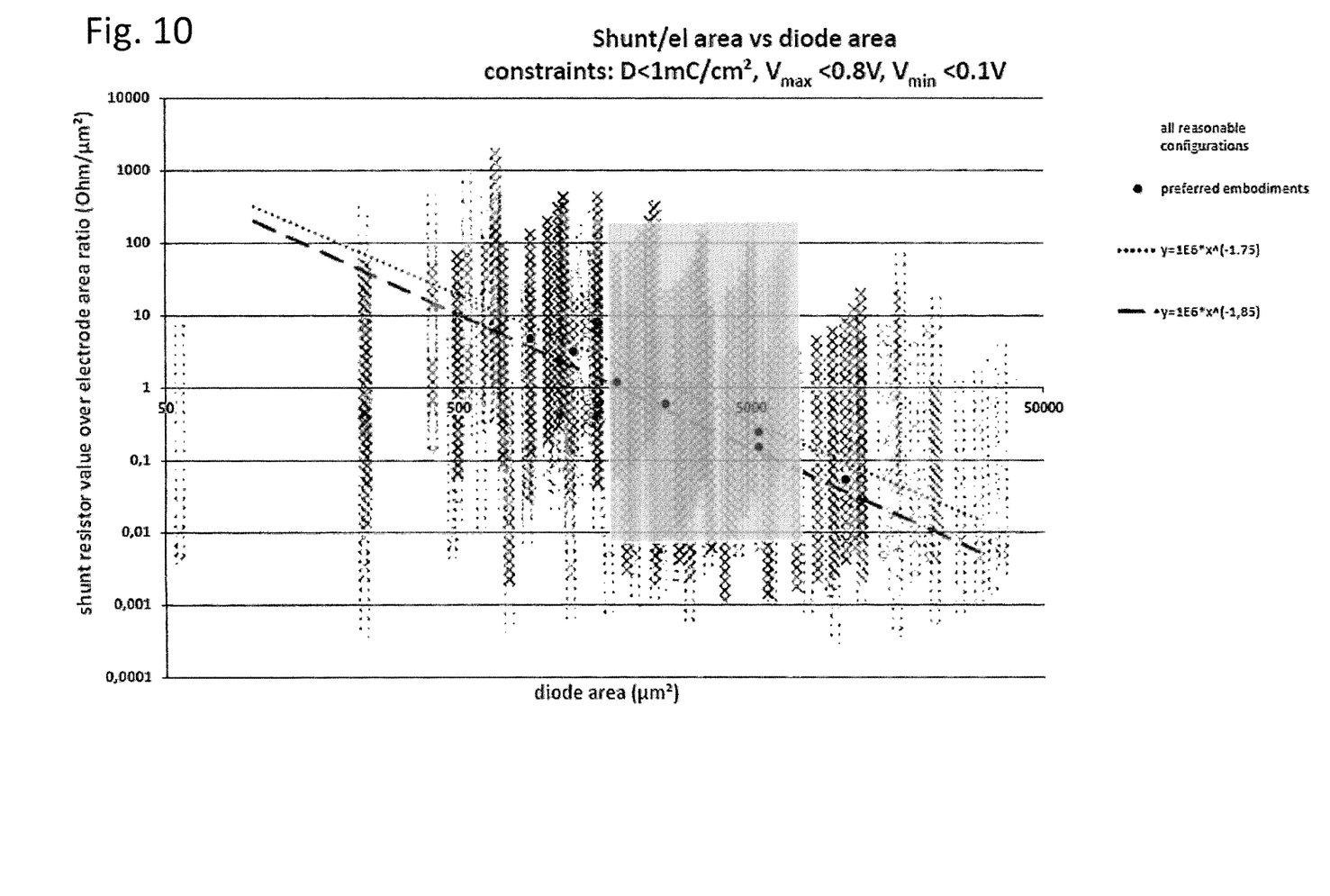

Similar to the diagram of FIG. 9, FIG. 10 shows a diagram with limiting lines resulting from different exponents n. An upper limit herein is defined by an exponent of n=−1.75 and a lower limit is defined by an exponent of n=−1.85.

It should be noted that the upper and the lower limit according to the above examples display the boundaries of ranges of possible parameter sets. That is to say that any parameter sets falling between those areas delimited by the lines representing the upper and lower value shall be considered to be part of the inventive idea to provide a pixel or pixel array with enhanced properties. It should further be noted that it is not an obvious choice for any skilled person to consider any such parameter combination, as it was the inventors acting to provide pixels and pixel arrays with multi-parameter adaptation by correlating the respective sizes of electrode, diode and resistance.

The invention claimed is:

1. A photosensitive implant comprising:
   at least one pixel having at least one diode,
   a stimulating electrode,
   a counter electrode, and
   a resistor, wherein a resistance of the resistor is chosen according to a predetermined relation of resistance, a size of the stimulating electrode, and a size of the diode, wherein a resistance of the resistor is determined by a formula:

$$R = a \cdot (D_{area}\hat{\ }n) \cdot E_{area}$$

wherein:
   R is a resistance of the resistor;
   $E_{area}$ is an electrode area of the stimulating electrode;
   $D_{area}$ is an effective diode area of the at least one diode;
   n is an exponent, n being in the range −2≤n≤−1.5, and
   a is a non-zero positive constant, wherein a is in the range 3·10$^5$≤a≤2·10$^6$.

2. The photosensitive implant according to claim 1, wherein a size of the stimulating electrode and a size of the at least one diode is represented as an area of the stimulating electrode and the at least one diode, respectively.

3. The photosensitive implant according to claim 1, wherein a size of the at least one diode is an effective diode size represented by a ratio of a total diode size, including a total diode area, and a number of diodes in the at least one pixel.

4. The photosensitive implant according to claim 1, wherein the electrode area is chosen such that, for any predetermined photosensitive diode area, the constant a is chosen from an interval $[7\cdot 10^5; 1.5\cdot 10^6]$, or the constant a fulfils $a=10^6$.

5. The photosensitive implant according to claim 1, wherein the electrode area is chosen such that, for any predetermined photosensitive diode area, the exponent n is chosen from an interval $[-1.75; -1.85]$ or n fulfils $n=-1.81$.

6. The photosensitive implant according to claim 1, wherein the exponent n fulfils $n=-1.81$ and wherein the constant a is chosen from an interval $[3\cdot 10^5; 2\cdot 10^6]$, or from an interval $[7\cdot 10^5; 1.5\cdot 10^6]$.

7. The photosensitive implant according to claim 1, wherein the constant a fulfils $a=10^6$ and wherein the exponent n is chosen from an interval $[-1.5; -2]$, or from an interval $[-1.75; -1.85]$.

8. The photosensitive implant according to claim 1, wherein the counter electrode is arranged around the stimulating electrode and/or around the at least one diode.

9. The photosensitive implant according to claim 1, further comprising a plurality of pixels, which are arranged in a pixel array.

10. The photosensitive implant according to claim 1, wherein the at least one pixel has a substantially hexagonal shape.

11. The photosensitive implant according to claim 1, wherein the stimulating electrode has a substantially circular shape.

12. The photosensitive implant according to claim 1, wherein an electrode area in the at least one pixel is less than $100000\ \mu m^2$, or between $100\ \mu m^2$ and $10000\ \mu m^2$, or between approximately $500\ \mu m^2$ and $3300\ \mu m^2$.

13. The photosensitive implant according to claim 1, wherein the diode area is less than $100000\ \mu m^2$, or the diode area is between $50\ \mu m^2$ and $100000\ \mu m^2$, or the diode area is between $500\ \mu m^2$ and $10000\ \mu m^2$.

14. The photosensitive implant according to claim 1, wherein the implant is a subretinal implant.

15. A method for producing a photosensitive implant that includes at least one pixel having at least one diode, a stimulating electrode, a counter electrode, and a resistor, wherein a resistance of the resistor is chosen according to a predetermined relation of resistance, a size of the stimulating electrode, and a size of the diode, the method comprising:
providing a substrate; and
providing, on the substrate, a pixel structure, wherein the pixel structure comprises:
at least an electrode;
a diode; and
a resistor, wherein a resistance of the resistor is chosen according to a predetermined relation of resistance, a size of the stimulating electrode, and a size of the diode,
wherein, the resistance of the resistor is determined by the formula:

$R = a\cdot (D_{area}\char`\^ n)\cdot E_{area}$ wherein:
R is the resistance of the resistor;
$E_{area}$ is an electrode area of the stimulating electrode;
$D_{area}$ is an effective diode area of the at least one diode;
n is an exponent, n being in the range $-2\leq n\leq -1.5$, and
a is a non-zero positive constant, wherein a is in the range
$3\cdot 10^5 \leq a \leq 2\cdot 10^6$.

16. The method according to claim 15, wherein the size of the stimulating electrode and the size of the diode is represented as an area of the stimulating electrode and the diode, respectively and wherein the diode size is an effective diode size represented by a ratio of a total diode size that includes a total diode area, and a number of diodes in the pixel.

17. The method according to claim 15, wherein the electrode area is chosen such that, for any predetermined photosensitive diode area, the constant a is chosen from an interval $[7\cdot 10^5; 1.5\cdot 10^6]$, or the constant a fulfils $a=10^6$.

18. The method according to claim 15, wherein the electrode area is chosen such that, for any predetermined photosensitive diode area, the exponent n is chosen from an interval $[-1.75; -1.85]$ or n fulfils $n=-1.81$.

19. The method according to claim 15, wherein the exponent n fulfills $n=-1.81$ and wherein the constant a is chosen from an interval $[3\cdot 10^5; 2\cdot 10^6]$, or from the interval $[7\cdot 10^5; 1.5\cdot 10^6]$.

20. The method according to claim 15, wherein the constant a fulfils $a=10^6$ and wherein the exponent n is chosen from an interval $[-1.5; -2]$, or from the interval $[-1.75; -1.85]$.

21. The method according to claim 15, wherein an electrode area in at least one pixel is less than $100000\ \mu m^2$, or is between $100\ \mu m^2$ and $100000\ \mu m^2$, or is between approximately $500\ \mu m^2$ and $3300\ \mu m^2$.

22. The method according to claim 15, wherein a diode area is less than $100000\ \mu m^2$, or the diode area is between $50\ \mu m^2$ and $100000\ \mu m^2$, or the diode area is between $500\ \mu m^2$ and $10000\ \mu m^2$.

\* \* \* \* \*